United States Patent
Chan et al.

(10) Patent No.: US 11,672,797 B2
(45) Date of Patent: Jun. 13, 2023

(54) METHODS OF TREATING KELOIDS

(71) Applicant: Hampton University, Hampton, VA (US)

(72) Inventors: Joanne Chan, Hampton, VA (US); Jessica L. Richert, Newport News, VA (US)

(73) Assignee: Hampton University, Hampton, VA (US)

( * ) Notice: Subject to any disclaimer, the term of this patent is extended or adjusted under 35 U.S.C. 154(b) by 0 days.

(21) Appl. No.: 16/870,017

(22) Filed: May 8, 2020

(65) Prior Publication Data
US 2020/0352936 A1  Nov. 12, 2020

Related U.S. Application Data

(60) Provisional application No. 62/845,443, filed on May 9, 2019.

(51) Int. Cl.
| | |
|---|---|
| *A61K 31/495* | (2006.01) |
| *A61P 17/02* | (2006.01) |
| *A61K 31/198* | (2006.01) |
| *G01N 33/50* | (2006.01) |
| *A61K 31/18* | (2006.01) |
| *A61K 31/7004* | (2006.01) |

(52) U.S. Cl.
CPC ............ *A61K 31/495* (2013.01); *A61K 31/18* (2013.01); *A61K 31/198* (2013.01); *A61K 31/7004* (2013.01); *A61P 17/02* (2018.01); *G01N 33/5044* (2013.01)

(58) Field of Classification Search
CPC .... A61K 31/495; A61K 31/18; A61K 31/198; A61K 31/7004; A61P 17/02; G01N 33/5044
USPC .......................................................... 514/23
See application file for complete search history.

(56) References Cited

U.S. PATENT DOCUMENTS

| | | | |
|---|---|---|---|
| 6,670,330 B1 | 12/2003 | Lampidis et al. | |
| 2012/0070369 A1* | 3/2012 | Iliopoulos | A61K 31/366 424/1.11 |

OTHER PUBLICATIONS

Glossary of medical education terms, Institute of International Medical Education. http://www.iime.org/glossary.htm Accessed in Mar. 2013. (Year: 2013).*
Richert-Jones et al. Targeting Keloid Fibroblasts by Inhibition of Hypoxia Signaling. J Clin Investigat Dermatol. 2020;8(2): 5. (Year: 2020).*
Li et al. Metabolic reprogramming in keloid fibroblasts: Aerobic glycolysis and a novel therapeutic strategy. Biochemical and Biophysical Research Communications 496 (2018) 641e647. (Year: 2018).*
Audrito, Valentina, et al. "PD-L1 up-regulation in melanoma increases disease aggressiveness and is mediated through miR-17-5p." Oncotarget 8.9 (2017): 15894.
Babu, Mary, Robert Diegelmann, and Noelynn Oliver. "Keloid fibroblasts exhibit an altered response to TGF-β." J Invest Dermatol 99 (1992): 650-655.
Ban, Hyun Seung, et al. "Identification of targets of the HIF-1 inhibitor IDF-11774 using alkyne-conjugated photoaffinity probes." Bioconjugate chemistry 27.8 (2016): 1911-1920.
Becker, Kimberly A., and John J. Jones. "An emerging treatment alternative for anemia in chronic kidney disease patients: a review of Daprodustat." Advances in therapy 35.1 (2018): 5-11.
Curtis, Kelly K., William W. Wong, and Helen J. Ross. "Past approaches and future directions for targeting tumor hypoxia in squamous cell carcinomas of the head and neck." Critical reviews in oncology/hematology 103 (2016): 86-98.
DeadEnd™ Colorimetric TUNEL System, https://www.promega.com/Products/Cell-Health-Assays/Apoptosis-Assays/DeadEnd-Colorimetric-TUNEL-System/?fq=tunel&catNum=G7360 (accessed on May 12, 2020).
Fearmonti, Regina, et al. "A review of scar scales and scar measuring devices." Eplasty 10 (2010).
Hanahan, Douglas, and Robert A. Weinberg. "Hallmarks of cancer: the next generation." cell 144.5 (2011): 646-674.
Jacoby, Jörg J., et al. "Treatment with HIF-1α antagonist PX-478 inhibits progression and spread of orthotopic human small cell lung cancer and lung adenocarcinoma in mice." Journal of Thoracic Oncology 5.7 (2010): 940-949.
Lu, Wensheng, et al. "SNP rs1511412 in FOXL2 gene as a risk factor for keloid by meta analysis." International journal of clinical and experimental medicine 8.2 (2015): 2766.
Mistry, Nikhil, et al. "Red blood cell antibody-induced anemia causes differential degrees of tissue hypoxia in kidney and brain." American Journal of Physiology-Regulatory, Integrative and Comparative Physiology 314.4 (2018): R611-R622.
Narita, Takuhito, et al. "Identification of a novel small molecule HIF-1α translation inhibitor." Clinical Cancer Research 15.19 (2009): 6128-6136.
RealTime-Glo™ Annexin V Apoptosis and Necrosis Assay, https://www.promega.com/Products/Cell-Health-Assays/Apoptosis-Assays/RealTime%20Glo%20Annexin%20V%20Apoptosis%20Assay/?fq=JA1000&catNum=JA1000 (accessed on May 12, 2020).
Shi, Chao, Jianyu Zhu, and Degang Yang. "The pivotal role of inflammation in scar/keloid formation after acne." Dermatoendocrinology 9.1 (2017): e1448327.
Si, Lou-Bin, et al. "Sensitization of keloid fibroblasts by quercetin through the PI3K/Akt pathway is dependent on Yegulation of HIF-1α." American journal of translational research 10.12 (2018): 4223.
Syed, Farhatullah, et al. "Keloid disease can be inhibited by antagonizing excessive mTOR signaling with a novel dual TORC1/2 inhibitor." The American journal of pathology 181.5 (2012): 1642-1658.

(Continued)

*Primary Examiner* — Yih-Horng Shiao
(74) *Attorney, Agent, or Firm* — Ice Miller LLP

(57) ABSTRACT

The present invention relates to methods of treating or inhibiting keloids in a subject with hypoxia-inducible factor-1 (HIF-1) inhibiting compounds, methods of screening or identifying compounds to induce cell death in keloids, and methods of inducing cell death in keloids.

11 Claims, 12 Drawing Sheets

(56) References Cited

OTHER PUBLICATIONS

Syed, Farhatullah, et al. "Potent dual inhibitors of TORC1 and TORC2 complexes (KU-0063794 and KU-0068650) demonstrate in vitro and ex vivo anti-keloid scar activity." Journal of Investigative Dermatology 133.5 (2013): 1340-1350.
Vincent, Annette S., et al. "Human skin keloid fibroblasts display bioenergetics of cancer cells." Journal of Investigative Dermatology 128.3 (2008): 702-709.
Werner, Sabine, Thomas Krieg, and Hans Smola. "Keratinocyte-fibroblast interactions in wound healing." Journal of Investigative Dermatology 127.5 (2007): 998-1008.
Zhao, Ying, et al. "NEDD4 single nucleotide polymorphism rs2271289 is associated with keloids in Chinese Han population." American journal of translational research 8.2 (2016): 544.
Zhu, Fei, et al. "Association study confirmed susceptibility loci with keloid in the Chinese Han population." PLoS One 8.5 (2013).

\* cited by examiner

METHODS OF TREATING KELOIDS

CROSS-REFERENCE TO PRIOR APPLICATION

This application claims priority to and the benefit thereof from U.S. Provisional Application No. 62/845,443, filed May 9, 2019, titled "METHODS OF TREATING KELOIDS," the entirety of which is hereby incorporated herein by reference.

STATEMENT OF GOVERNMENT SUPPORT

This invention was made with government support under grant number AI102223 awarded by the National Institutes of Health. The government has certain rights in the invention.

FIELD OF THE INVENTION

The present invention relates to methods of treating or inhibiting keloids in a subject with hypoxia-inducible factor-1 (HIF-1)-inhibiting compounds, and methods of screening for compounds to induce cell death in keloids.

BACKGROUND

Keloids are raised scars that can form after an injury, such as an ear piercing, a severe burn, or surgery. They can occur anywhere on the body, but are more commonly found on the upper chest, shoulders, head, neck, upper back and earlobes. In severe cases, keloids can become extremely enlarged, compressing nearby tissues and limiting movement. In addition to physical impairment, keloids may also lead to disfigurement and psychological stress. See, Trace, A. P., et al., Am J Clin Dermatol, 17(3): p. 201-23 (2016). Keloids have been described in medical literature as a type of pathological scar that is refractory to treatment. The name "keloid" was introduced by the French surgeon, Dr. J. Alibert, using the Greek word "chele" (meaning pincer/claw), to describe the abnormal claw-like appearance of these lesions. See, Shi, C., et al., Dermatoendocrinol, 9(1): p. e1448327(2017). The etiology of keloids remains unknown. An early comprehensive report by Dr. Louis Tiffany in 1887 essentially describes keloids as we know them today, noting that individuals of African descent are predisposed to keloid formation. See, Tiffany, L. M., Transactions of the American Surgical Association, V: p. 262-273 (1887).

Research over the last 30 years has confirmed that the higher incidence of keloid disease occurs among skin of color individuals (e.g. persons of African, Hispanic, and Asian descent. See, Shih, B. et al., Arch Dermatol Res, 302(5): p. 319-39 (2010); Shih, B., et al., Wound Repair Regen, 18(2): p. 139-53 (2010).

Efforts by researchers across the globe have identified common single nucleotide polymorphisms (SNPs) in genome-wide association studies (GWAS) in Han Chinese, Japanese and African American keloid patients. See, Nakashima, M., et al., Nat Genet, 42(9): p. 768-71 (2010); Zhu, F., et al., PLoS One, 8(5): p. e62377 (2013); Lu, W., et al., Int J Clin Exp Med, 2015. 8(2): p. 2766-71; Velez Edwards, D. R., et al., Hum Genet, 133(12): p. 1513-23 (2014); Zhao, Y., et al., Am J Transl Res, 8(2): p. 544-55 (2016). Common SNPs have been identified from patients living in distinct geographic locations, suggesting a similar disease pathogenesis. Thus, identification of the molecular drivers and therapeutic targets of keloid progression in one group is likely to also be useful for keloid patients across the globe.

It is well established that keloids should not be surgically removed because of their tendency for recurrence. Beginning around the 1960's, clinicians have applied a number of treatments to help keloid patients, including pressure, cryotherapy, intralesional steroid injections and chemotherapy, but none have obtained satisfactory results, owing to the induction of secondary keloid(s) at the injury site. See, Trace, A. P., et al., Am J Clin Dermatol, 17(3): p. 201-23 (2016); Mari, W., et al., Novel Insights on Understanding of Keloid Scar: Article Review. J Am Coll Clin Wound Spec, 7(1-3): p. 1-7 (2015).

There is a need for effective therapeutic treatments to eliminate or reduce the size of existing keloids, to prevent the formation of keloids or to prevent their recurrence after treatment, and for methods to identify inhibitors of keloids.

SUMMARY OF INVENTION

In certain embodiments, the present invention relates to a method of treating keloids in a subject comprising administering to the subject a therapeutically effective amount of a hypoxia-inducible factor-1 alpha (HIF-1)-inhibiting compound that induces cell death in keloids. In certain embodiments, the HIF-1 inhibiting compound is selected from the group consisting of N,N'-(Dithiodi-2,1-ethanediyl)bis[2,5-dichlorobenzenesulfonamide (hereinafter designated "KC7F2"); 2-(4-((3r,5r,7r)-adamantan-1-yl)phenoxy)-1-(4-methylpiperazin-1-yl)ethan-1-one (hereinafter designated "IDF-11774"); and (S)-4-(2-amino-2-carboxyethyl)-N,N-bis(2-chloroethyl)aniline oxide dihydrochloride (hereinafter designated "PX-478"), and a pharmaceutically acceptable salt thereof.

In certain embodiments, the HIF-1 inhibiting compound is administered in a composition further comprising at least one excipient or pharmaceutical carrier.

In certain embodiments, the method of treating keloids further comprises administering a glycolysis inhibitor. In certain embodiments, the glycolysis inhibitor is 2-deoxyglucose (2-DG).

In certain embodiments, the present invention relates to a method of screening or identifying a compound to induce cell death in keloids, said method comprising:
(a) incubating with keloid fibroblasts a compound to be tested, a glycolysis-inhibiting compound, both the test compound and the glycolysis-inhibiting compound, and a control;
(b) adding at least one stain to the keloid fibroblasts of step (a) to detect dying fibroblasts;
(c) detecting the stained dying fibroblasts of step (b);
(d) comparing the stained dying keloid fibroblasts incubated with the test compound, with the glycolysis-inhibiting compound, and with both the test compound and the glycolysis-inhibiting compound to the stained dying control keloid fibroblasts of step (c),
wherein an increase in the number of stained dying fibroblasts incubated with the test compound, a glycolysis-inhibiting compound, or both the test compound and the glycolysis-inhibiting compound compared to the stained control dying fibroblasts indicates the compound can induce cell death in keloids.

In certain embodiments, the incubating of step (a) may be up to sixteen hours. In certain embodiments, the at least one stain of step (b) is a fluorescent dye. In certain embodiments, the fluorescent dye of step (b) is Hoechst or propidium iodide or both Hoechst and propridium iodide.

In certain embodiments, the present invention relates to a method of inducing cell death in keloids comprising contacting the keloids with a hypoxia-inducible factor-1 alpha (HIF-1)-inhibiting compound in an amount effective to induce cell death in the keloids. In certain embodiments, the HIF-1 inhibiting compound is selected from the group consisting of KC7F2, IDF-11774 and PX-478.

In certain embodiments, the method of inducing cell death in keloids further comprises contacting the keloids with a glycolysis inhibitor in an amount effective to induce cell death in the keloids. In certain embodiments, the glycolysis inhibitor is 2-deoxyglucose (2-DG).

Other aspects and advantages of the present invention are described further in the following detailed description of the preferred embodiments thereof.

BRIEF DESCRIPTION OF THE DRAWINGS

The accompanying figures which are incorporated in and constitute a part of this specification, illustrate several aspects and together with the description serve to explain the principles of the invention. However, the disclosure is not limited to the precise arrangements and instrumentalities of the embodiments depicted in the drawings.

FIG. 1A. shows an ear keloid, after ear piercings (Courtesy of Dr. Joe Niamtu, Facial Scars and Keloids Richmond Va.).

FIG. 1B shows a child with severe chest and facial keloid after a burn injury (Gillies McIndoe Research Institute Newsletter, March, 2016). FIG. 1C shows a chest keloid after heart surgery (image modified from Atwal et al., Am J Med Genet A, Vol. 170A(4): p. 891-5. (2016)). FIG. 1D shows a child in Africa with keloids in 1887 (Tiffany, L. M., Transactions of the American Surgical Association, 1887. V: p. 262-273).

FIG. 2A shows that cellular defects permit keloids to grow slowly and avoid apoptosis. FIG. 2B shows molecular defects in KFs suggest that targeting with clinical/preclinical cancer drugs may be effective. Checkboxes indicate novel molecular defects supported by the analysis described herein.

FIGS. 4A-B show the results on keloid fibroblasts, with the top panels (A-D, I-J) and the bottom panels (A'-D', I'-J') representing the same location within the well. In the top panels (A-D, I-J), cell nuclei were labelled with Hoechst and in the bottom panels (A'-D', I'-J'), dying cells were labelled with propridium iodide. Results are shown for keloid fibroblast cells untreated as the control (A, A'); treated with 40 µM HIF inhibitor KC7F2 (B, B'); treated with 10 mM glycolysis inhibitor 2-deoxyglucose (2-DG) (C, C'); treated with both 40 µM of KC7F2 and 10 mM of 2-DG (D, D'); treated with 25 µM IDF inhibitor IDF-11774 (I, I'); and treated with 25 uM PX-478 inhibitor (J, J'). FIGS. 4C-D show the results on normal cell fibroblasts, with, the top panels (E-H, K-L) and the bottom panels (E'-H', K'-L') representing the same location within the well. In the top panels (E-H, K-L), cell nuclei were labelled with Hoechst and in the bottom panels (E'-H', K'-L'), dying cells were labelled with propridium iodide. Results are shown for normal fibroblast cells untreated as the control (E, E'); treated with 40 µM HIF inhibitor KC7F2 (F, F'); treated with 10 mM glycolysis inhibitor 2-deoxyglucose (2-DG) (G, G'); treated with both 40 µM of KC7F2 and 10 mM of 2-DG (H, H'); treated with 25 uM IDF inhibitor IDF-11774 (K, K'); and treated with 25 uM PX-478 inhibitor (L, L').

In FIGS. 5A and 5B, the results on keloid fibroblasts (FIG. 5A) and normal fibroblasts (FIG. 5B) are shown in the top panels and the bottom panels, which are labelled CON, KC7F2, 2DG, and 2DG+KC7F2 and represent the same location within the well. In the top panels, 10,000 cells per well were stained with phalloidin for filamentous actin, and in the bottom panels, cells were stained with DAPI (4',6-diamidino-2-phenylindolepropridium iodide) to indicate dying cells. CON is for the control untreated cells; KC7F2 is for cells treated with 40 µM HIF inhibitor KC7F2; 2-DG is for cells treated with 10 mM glycolysis inhibitor 2-deoxyglucose (2-DG); 2DG+KC7F2 is for cells treated with both 40 µM of KC7F2 and 10 mM of 2-DG. The images were magnified four times.

In FIGS. 6A and 6B, the results on keloid fibroblasts (FIG. 6A) and normal fibroblasts (FIG. 6B) are shown in the top panels and the bottom panels, which are labelled CON, KC7F2, 2DG, and 2DG+KC7F2 and represent the same location within the well. In the top panels, 10,000 cells per well were stained with phalloidin for filamentous actin, and in the bottom panels, cells were stained with DAPI (4',6-diamidino-2-phenylindolepropridium iodide) to indicate dying cells. CON is for the control untreated cells; KC7F2 is for cells treated with 40 µM HIF inhibitor KC7F2; 2-DG is for cells treated with 10 mM glycolysis inhibitor 2-deoxyglucose (2-DG); 2DG+KC7F2 is for cells treated with both 40 µM of KC7F2 and 10 mM of 2-DG. The images were magnified ten times.

In FIGS. 7A and 7B, the results on keloid fibroblasts (FIG. 7A) and normal fibroblasts (FIG. 7B) are shown in the top panels and the bottom panels, which are labelled CON, KC7F2, 2DG, and 2DG+KC7F2 and represent the same location within the well. In the top panels, 20,000 cells per well were stained with phalloidin for filamentous actin, and in the bottom panels, cells were stained with DAPI (4',6-diamidino-2-phenylindolepropridium iodide) to indicate dying cells. CON is for the control untreated cells; KC7F2 is for cells treated with 40 µM HIF inhibitor KC7F2; 2-DG is for cells treated with 10 mM glycolysis inhibitor 2-deoxyglucose (2-DG); 2DG+KC7F2 is for cells treated with both 40 µM of KC7F2 and 10 mM of 2-DG. The images were magnified four times.

In FIGS. 8A and 8B, the results on keloid fibroblasts (FIG. 8A) and normal fibroblasts (FIG. 8B) are shown in the top panels and the bottom panels, which are labelled CON, KC7F2, 2DG, and 2DG+KC7F2 and represent the same location within the well. In the top panels, 20,000 cells per well were stained with phalloidin for filamentous actin, and in the bottom panels, cells were stained with DAPI (4',6-diamidino-2-phenylindolepropridium iodide) to indicate dying cells. CON is for the control untreated cells; KC7F2 is for cells treated with 40 µM HIF inhibitor KC7F2; 2-DG is for cells treated with 10 mM glycolysis inhibitor 2-deoxyglucose (2-DG); 2DG+ KC7F2 is for cells treated with both 40 µM of KC7F2 and 10 mM of 2-DG. The images were magnified ten times.

DETAILED DESCRIPTION

The present invention relates to the treatment of keloids, raised scars that extend beyond the boundaries of the original skin injury, leading to disfigurement, psychological stress and in severe cases, physical impairment. In particular, the invention pertains to the use of chemicals that alter the function of HIF-1 protein complexes, either used alone or in combination with additional medicines. This treatment may be used to prevent the formation of keloids, to prevent recurrence after treatment or to eliminate or reduce the size of existing keloids.

Present day treatments are not effective in treating keloids. Although keloid scars begin with skin injury, the process of wound healing is disrupted. See, Sun, L. M., et al., Arch Dermatol Res, 306(9): p. 803-8 (2014). Normal cutaneous healing requires formation of the myofibroblast, a transient cell type that contributes to the deposition of collagen and extracellular matrix proteins (ECM) into the wound. When healing is complete, the myofibroblast disappears through the process of apoptosis. Keloids, on the other hand, typically continue to enlarge over time. The center of the keloid scar consists of an excessive amount of collagen and extracellular matrix (ECM) proteins, deposited in a disorganized manner. See, Robles, D. T. et al., Clin Dermatol, 25(1): p. 26-32 (2007); Werner, S., et al., J Invest Dermatol, 127(5): p. 998-1008 (2007); Arwert, E. N., et al., Nat Rev Cancer, 12(3): p. 170-80 (2012); Audrito, V., et al., Oncotarget, 8(9): p. 15894-15911 (2017). These proteins are continuously produced by the keloid fibroblast (hereinafter "KF"), an abnormal cell continuously promoting fibrogenesis. In addition, KFs do not undergo apoptosis and are responsible for the persistent enlargement and fibrogenetic nature of keloid scars. Owing to the central role of KFs, cell-based studies on keloids have relied on information generated from patient-derived KF cells grown in culture as a model for study.

Figures 1A, 1B, 1C, 1D:
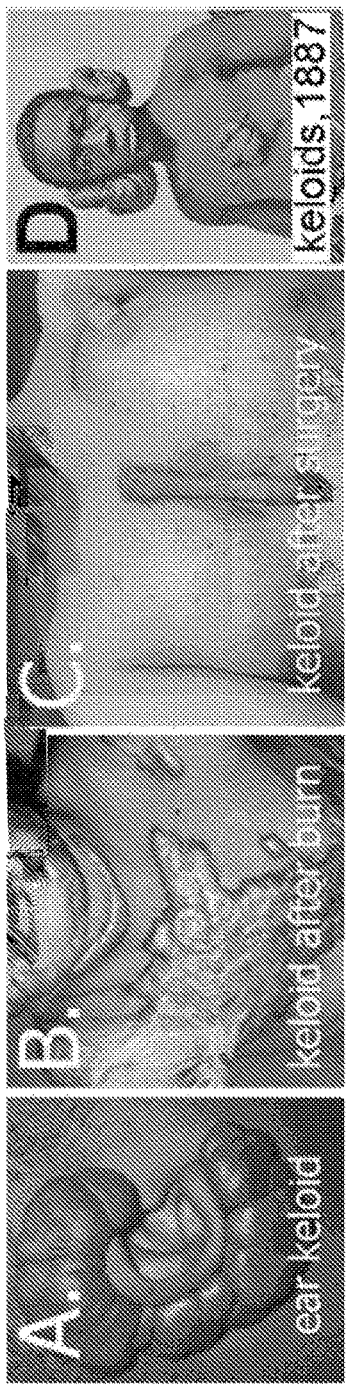
FIGS. 1A-D are pictures of patients with different types of keloids.
Figure 2B:
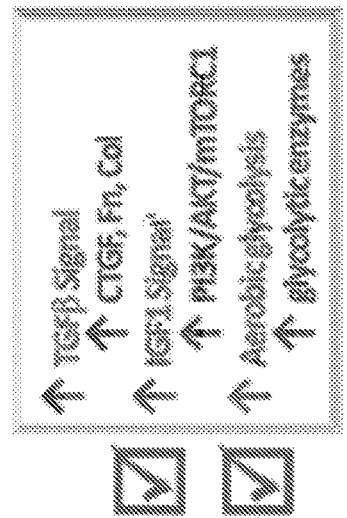
FIGS. 2A-B are diagrams showing keloid fibroblasts (KFs) recapitulating many features of keloids in vivo.
Figure 2A:
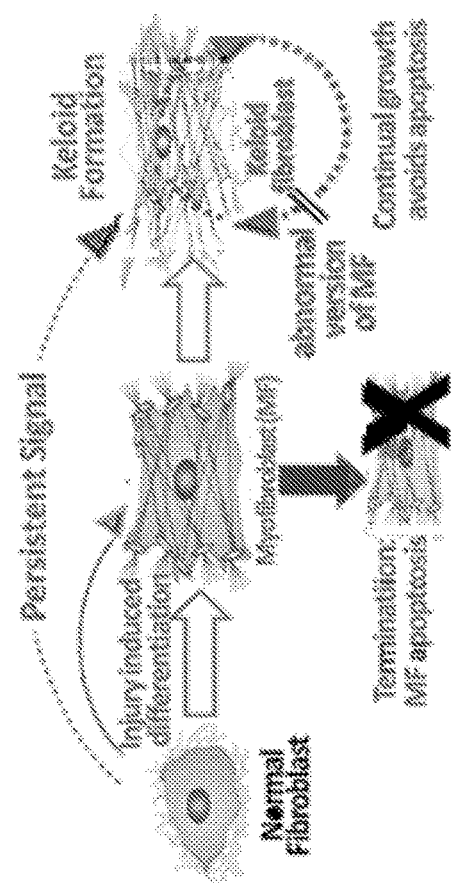

Several defining features have been observed in keloids or isolated KFs, illustrated in FIG. 2A-B. They include the overactivation of the TGFβ1 signaling pathway, which promotes the expression of collagens and ECM proteins, an overactivation of the mTORC1 pathway and a change in energy metabolism to favor glycolysis despite the availability of oxygen. See, Babu, M., et al., J Invest Dermatol, 99(5): p. 650-5 (1992); Bettinger, D. A., et al., Plast Reconstr Surg, 98(5): p. 827-33 (1996); Syed, F., et al., J Invest Dermatol, 133(5): p. 1340-50 (2013); Syed, F., et al., Am J Pathol, 181(5): p. 1642-58 (2012); Li, Q., et al., Biochem Biophys Res Commun, 496(2): p. 641-647 (2018); Vincent, A. S., et al., J Invest Dermatol, 128(3): p. 702-9 (2008).

Keloids display some but not all of the hallmarks with cancer progression, as proposed by Weinberg and Hanahan in Cell, 144(5): p. 646-74 (2011). Keloids have cellular defects that permit keloids to grow slowly and avoid apoptosis as shown in FIG. 2A. Without being limited to a theory, it is hypothesized that alteration(s) in a key master regulator might be responsible for a large portion of the observed KF characteristics reported by other researchers. The transcriptional activator Hypoxia-inducible factor (HIF)-1, for example, regulates the expression of genes involved in angiogenesis, cellular energy metabolism, and cell survival during cancer development. In most solid tumors the increased expression of HIF-1 is associated with poor prognoses and therapeutic outcomes. Therefore, HIF has been recognized as an attractive target for cancer therapy, and many HIF inhibitors have been reported. In addition, HIF estimates angiogenesis through the transcriptional activation of erythropoietin (EPO) and the Vascular endothelial growth factor (VEGF), originally known as vascular permeability factor (VPF). This component of HIF function has been under development for treatment of anemia, resulting from a number of diseases.

Generally speaking, HIF-1 can be viewed as a protective protein that is activated by cellular or organismal stresses. HIF-1 regulated genes then function to combat the initiating stress. HIF-1 function is altered in many human diseases including many solid tumors and in anemia. Small molecule chemical agents have been developed to modulate HIF-1 activity. HIF-1 transcriptional activity is enhanced in keloids. In keloid literature, a few studies using chemical agents and/or natural compounds on KFs, such as resveratrol and quercetin, have been shown to alter HIF-1 stability. See, Ikeda, K., et al., Wound Repair Regen,. 21(4): p. 616-23 (2013); Si, L. B., et al., Am J Transl Res, 10(12): p. 4223-4234 (2018). However, direct examination of HIF-1 chemical modulators on KFs has not been reported.

Hypoxia-inducible factor-1 (HIF-1) is a potent transcriptional regulator that is normally quiescent under physiological conditions. However, when cells and tissues are deprived of oxygen, or become hypoxic, HIF-1 activity is induced. A number of HIF-1 responsive genes are activated to eliminate the initial hypoxic stimulus. In human diseases, the HIF-1 pathway might become deregulated. For example, overactivation of the HIF-1 pathway could produce an overwhelming hypoxic effect that requires dampening while insufficient activation may require additional stimulation. For these reasons, chemical modulators of HIF-1 activity are being developed as potential therapeutic agents.

Figure 3:
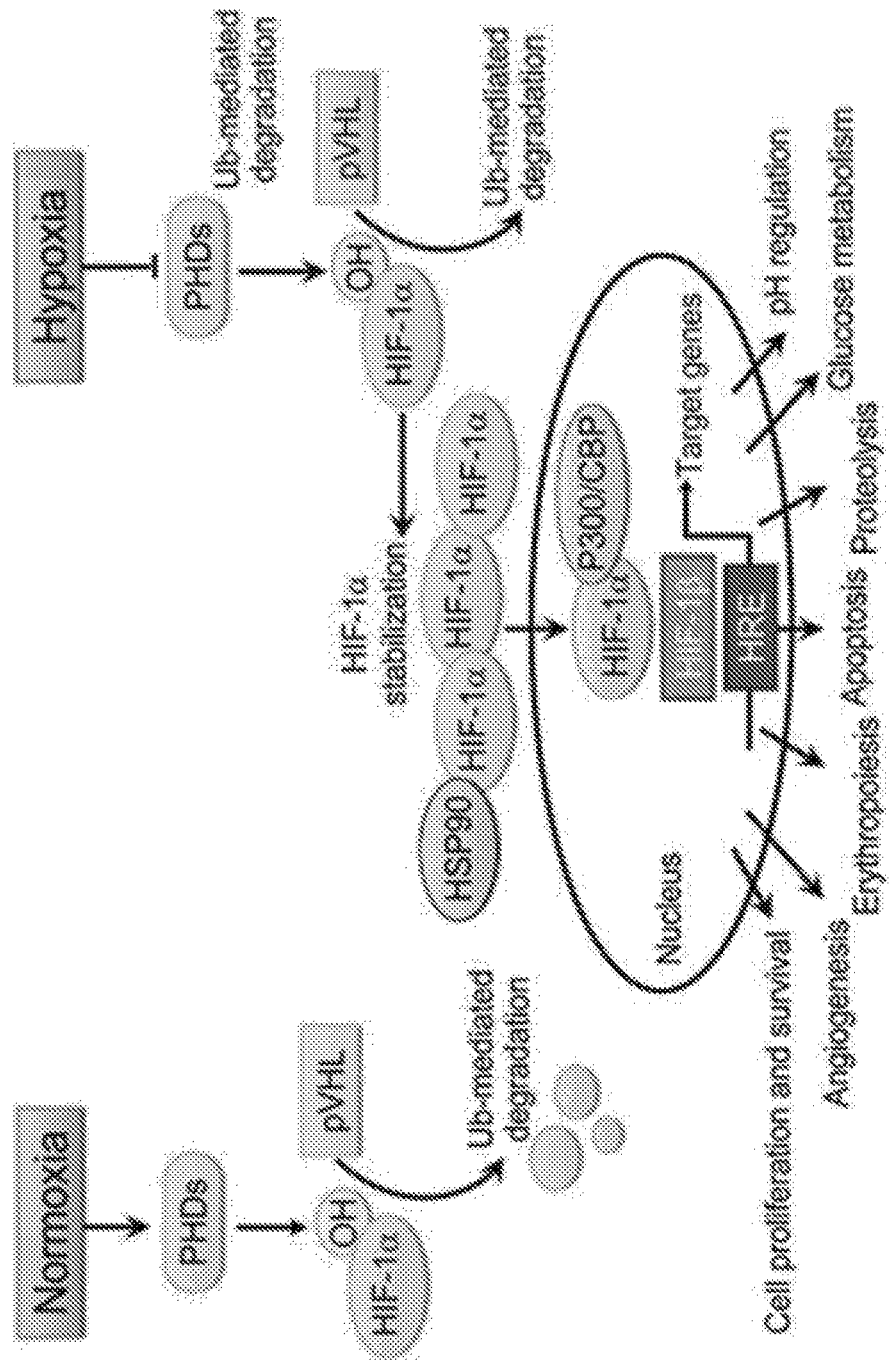
FIG. 3 shows a schematic of the hypoxia inducible factor-1 alpha (HIF-1α) pathway.
Figure 4A:
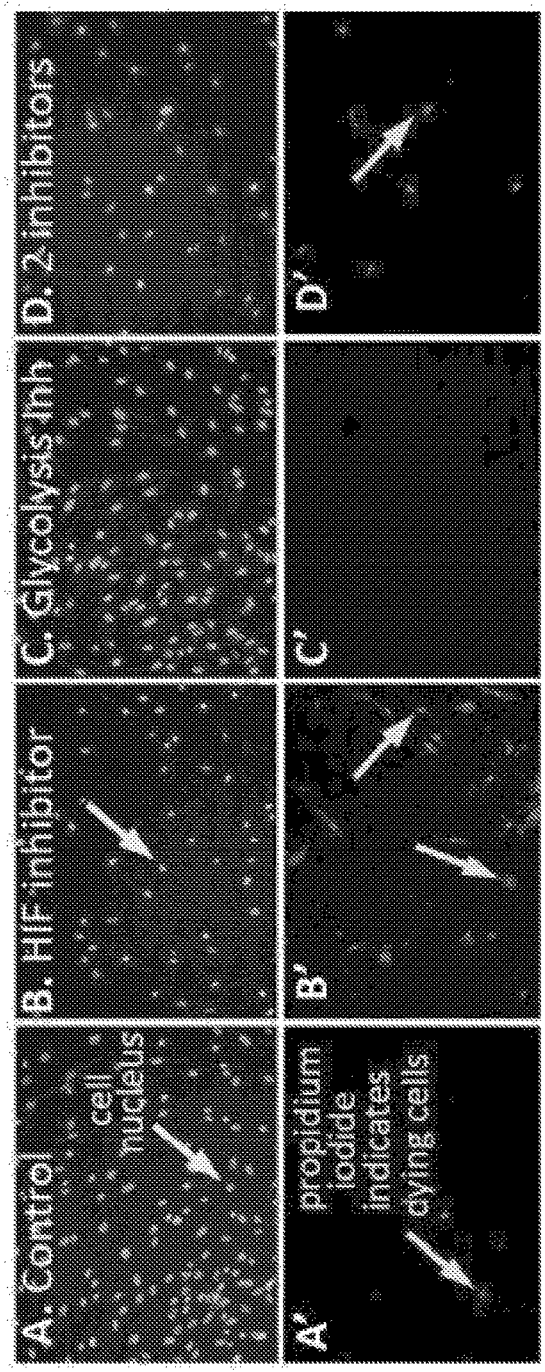
FIGS. 4A-D are fluorescent stained images showing assay results of a direct comparison between the actions of glycolytic versus HIF-1 inhibitors on keloid fibroblasts and normal fibroblasts.
Figure 4B:
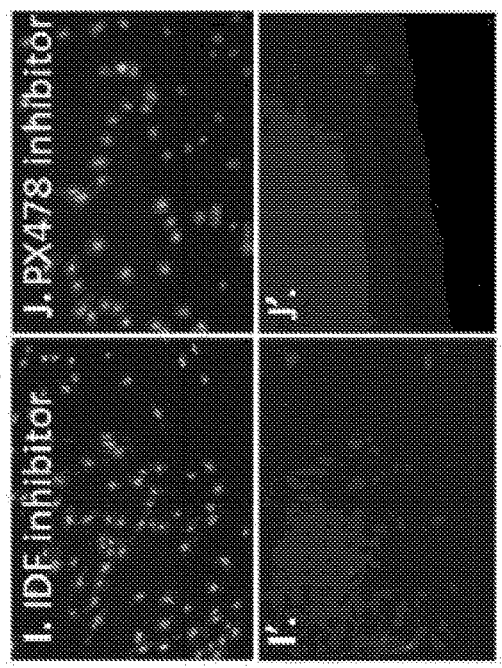
Figure 4C:
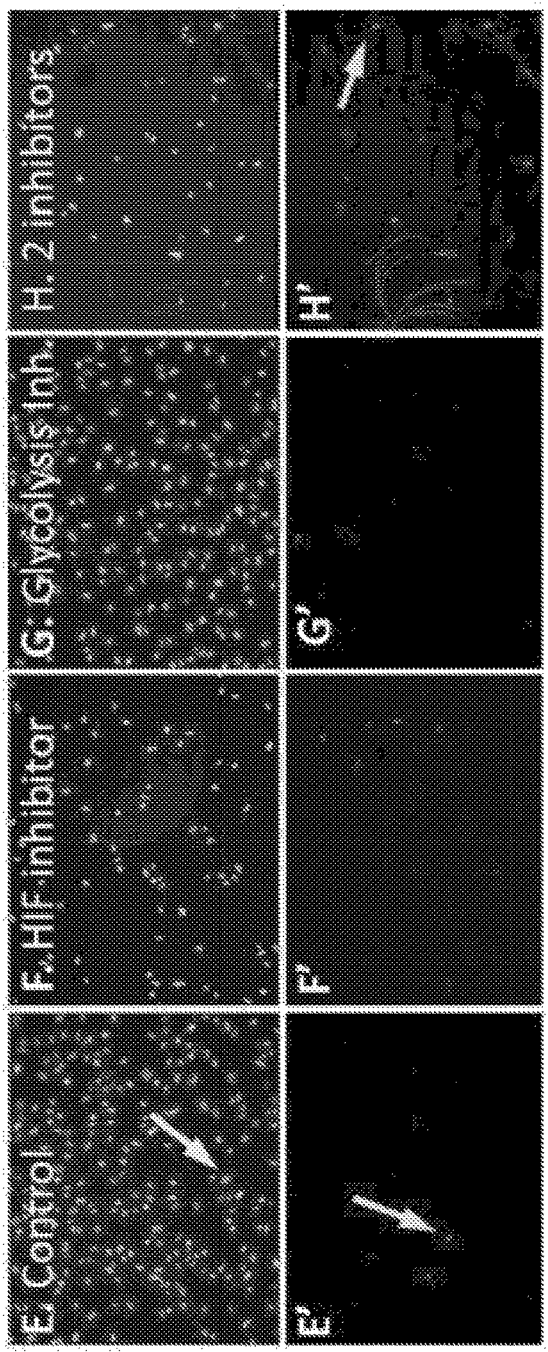
Figure 4D:
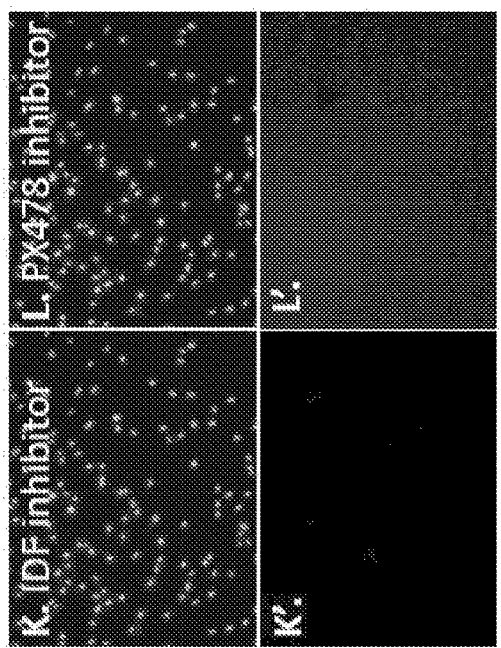
Figure 5A:
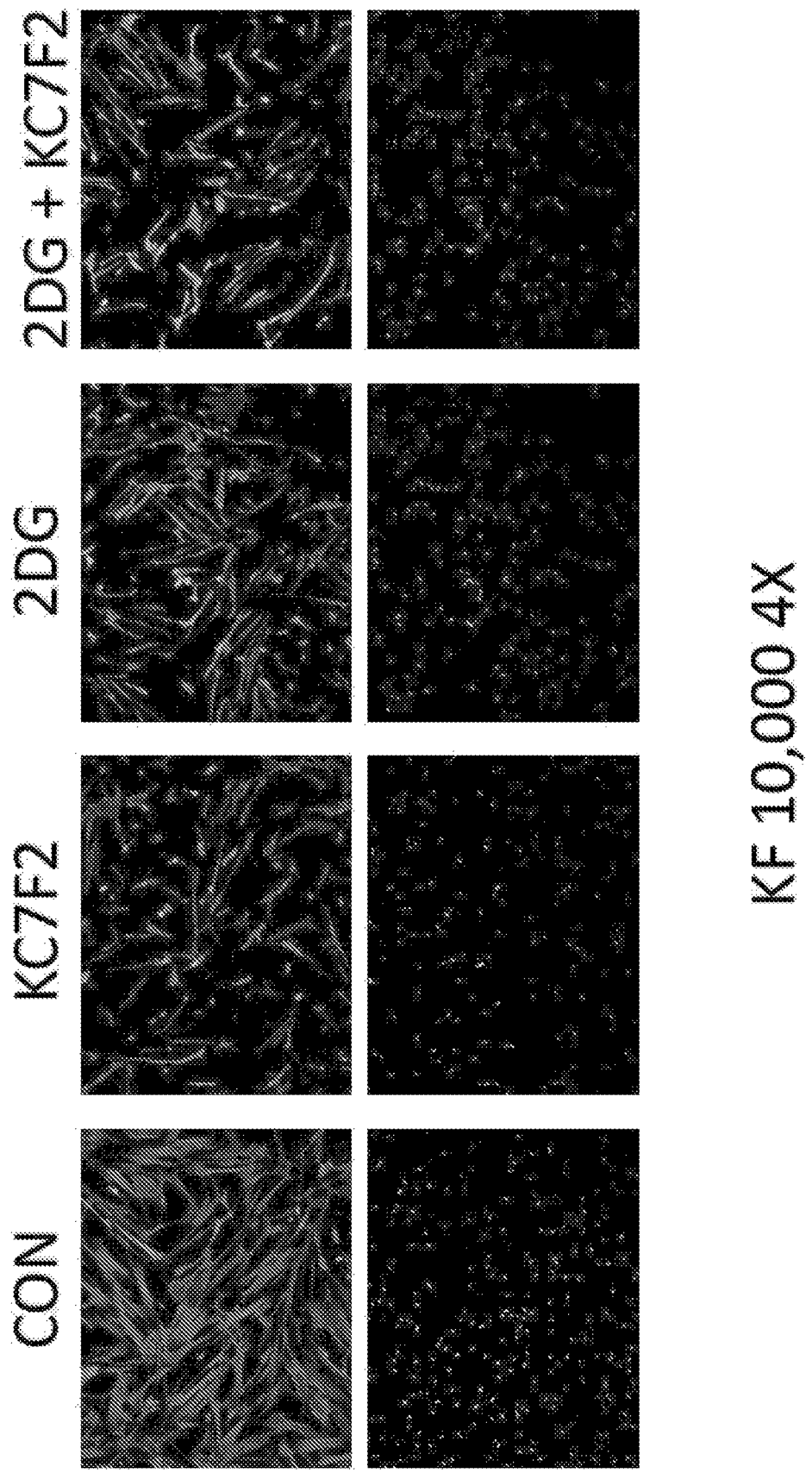
FIGS. 5A-B are fluorescent stained images showing assay results of a direct comparison between the actions of glycolytic versus HIF-1 inhibitors on keloid fibroblasts and normal fibroblasts.
Figure 5B:
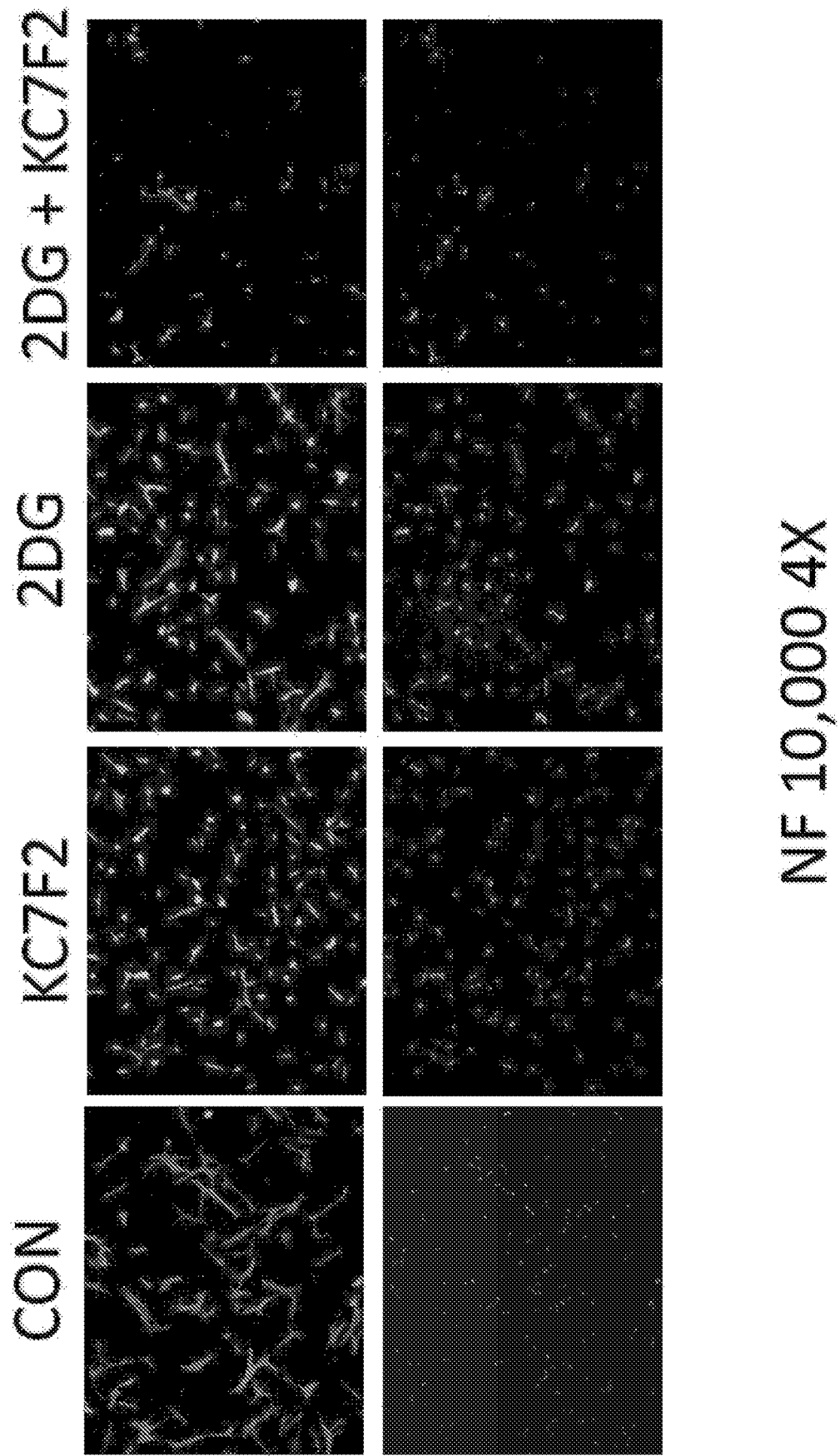
Figure 6A:
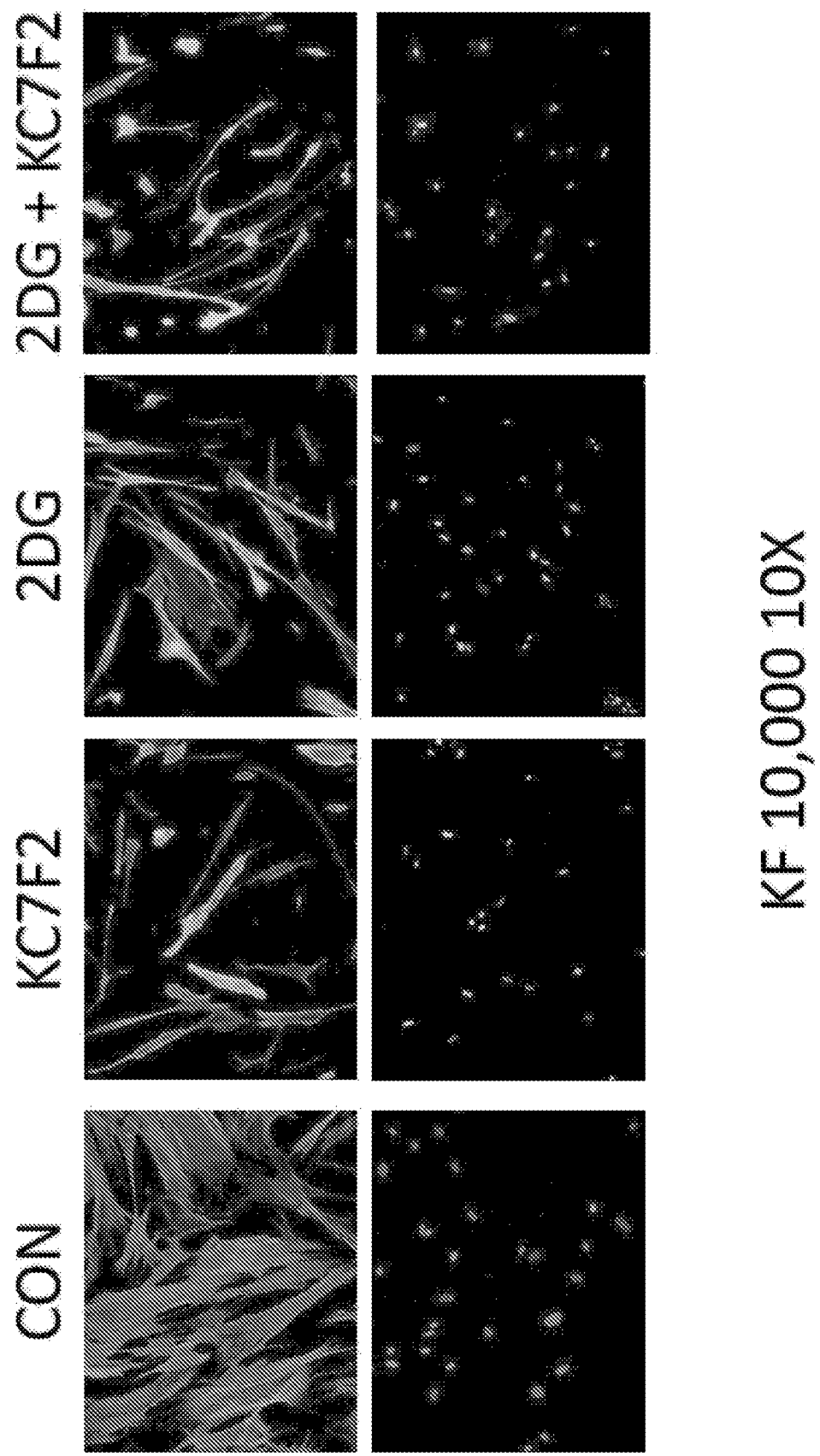
FIGS. 6A-B are fluorescent stained images showing assay results of a direct comparison between the actions of glycolytic versus HIF-1 inhibitors on keloid fibroblasts and normal fibroblasts.
Figure 6B:
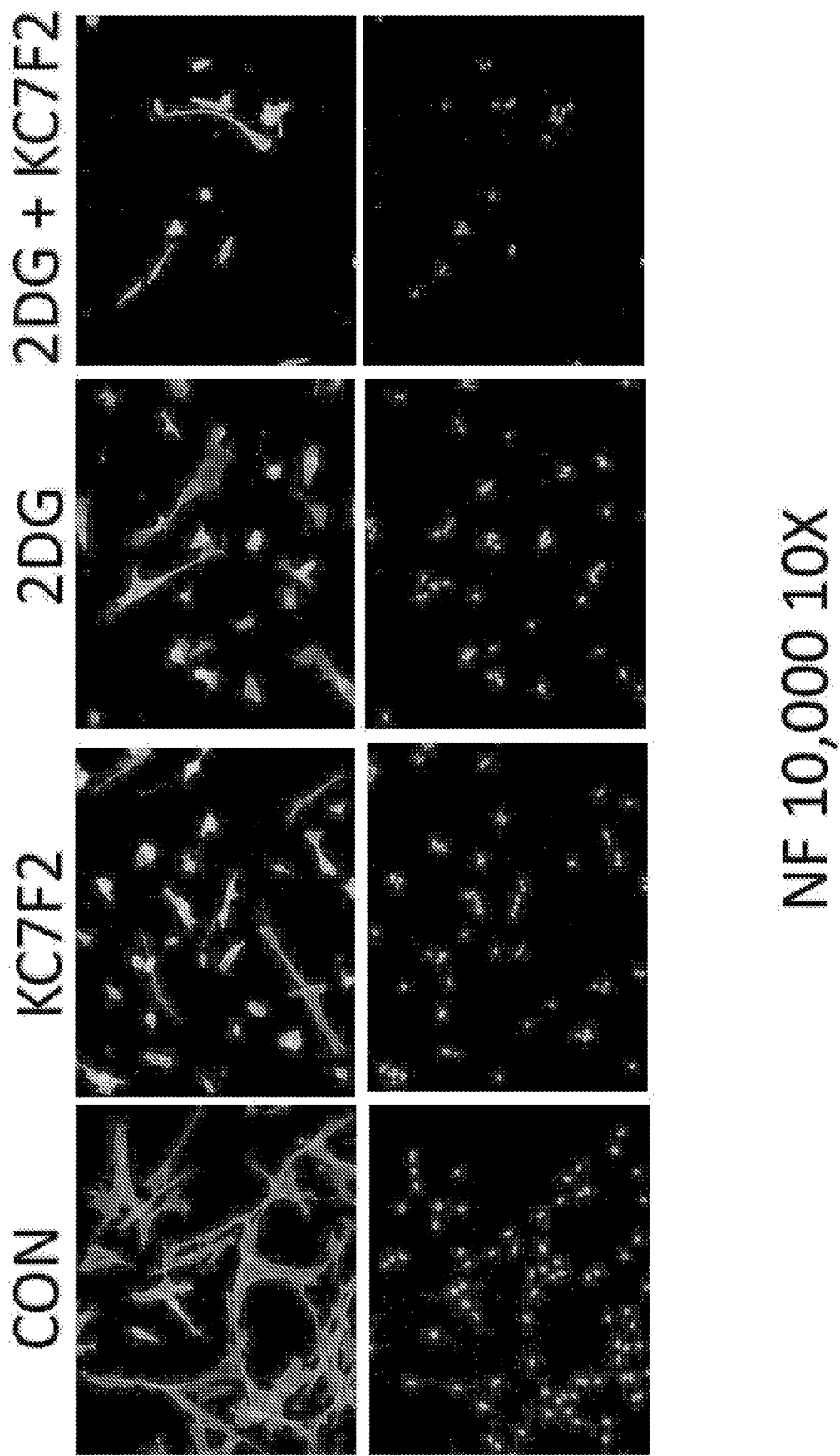
Figure 7A:
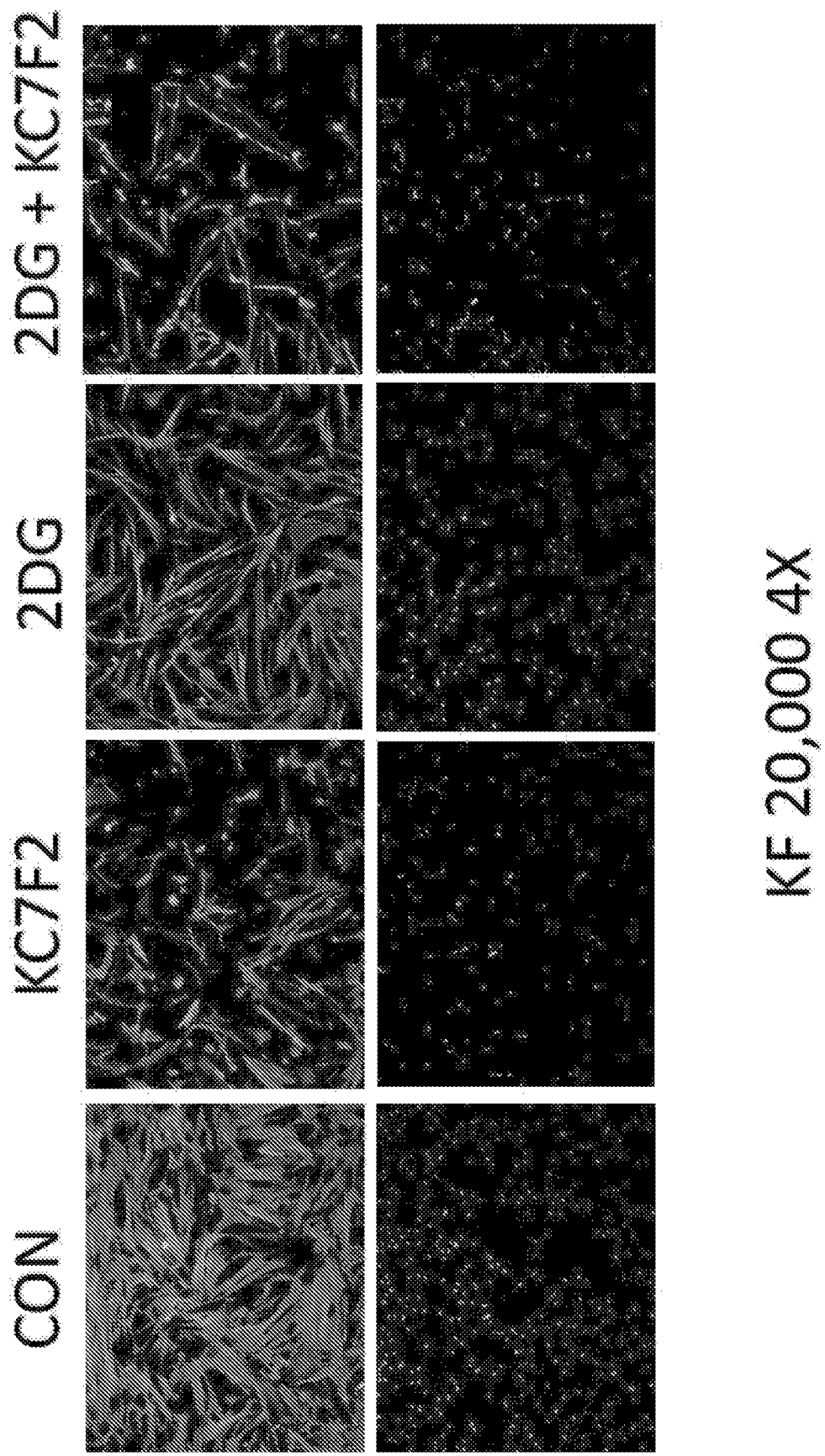
FIGS. 7A-B are fluorescent stained images showing assay results of a direct comparison between the actions of glycolytic versus HIF-1 inhibitors on keloid fibroblasts and normal fibroblasts.
Figure 7B:
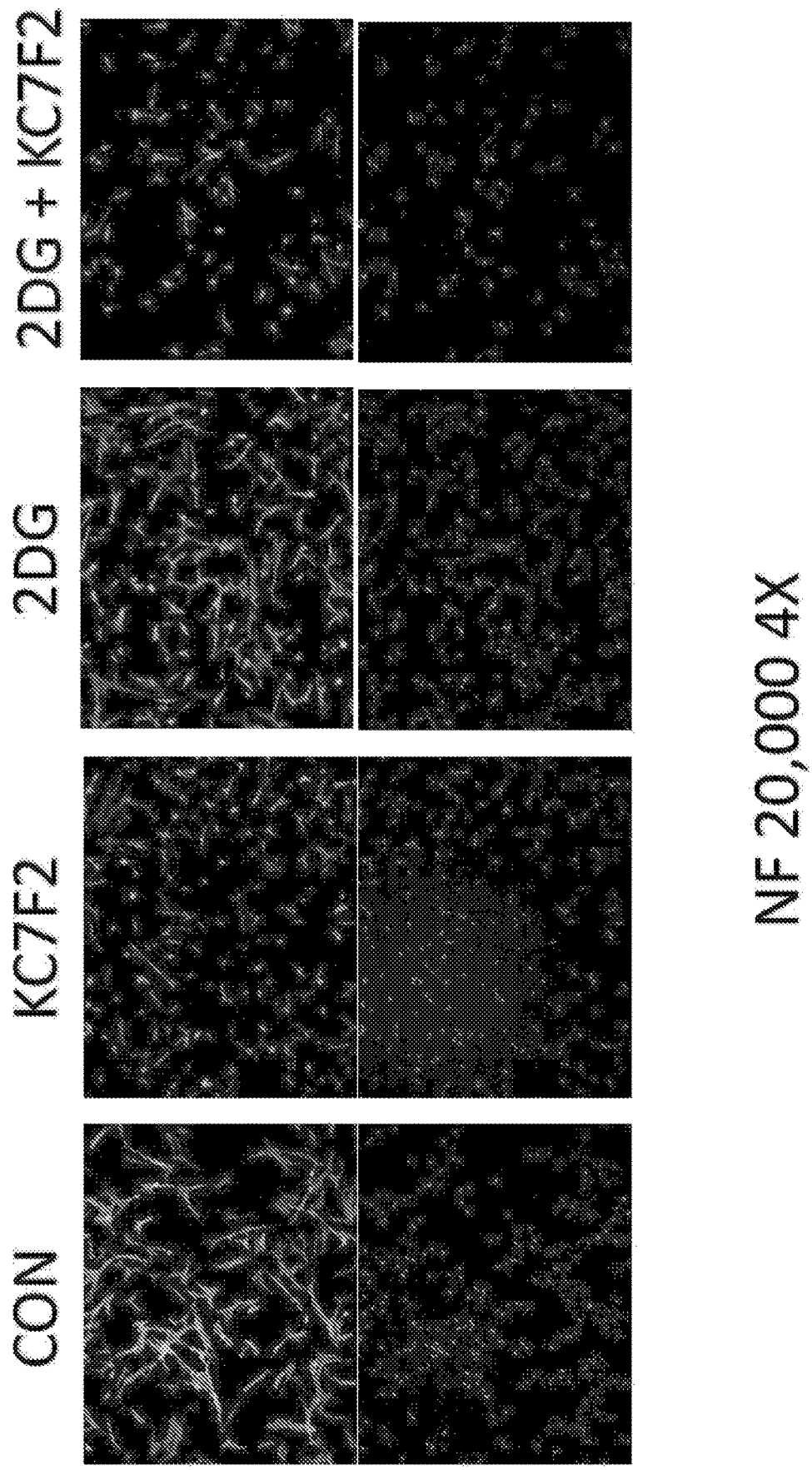
Figure 8A:
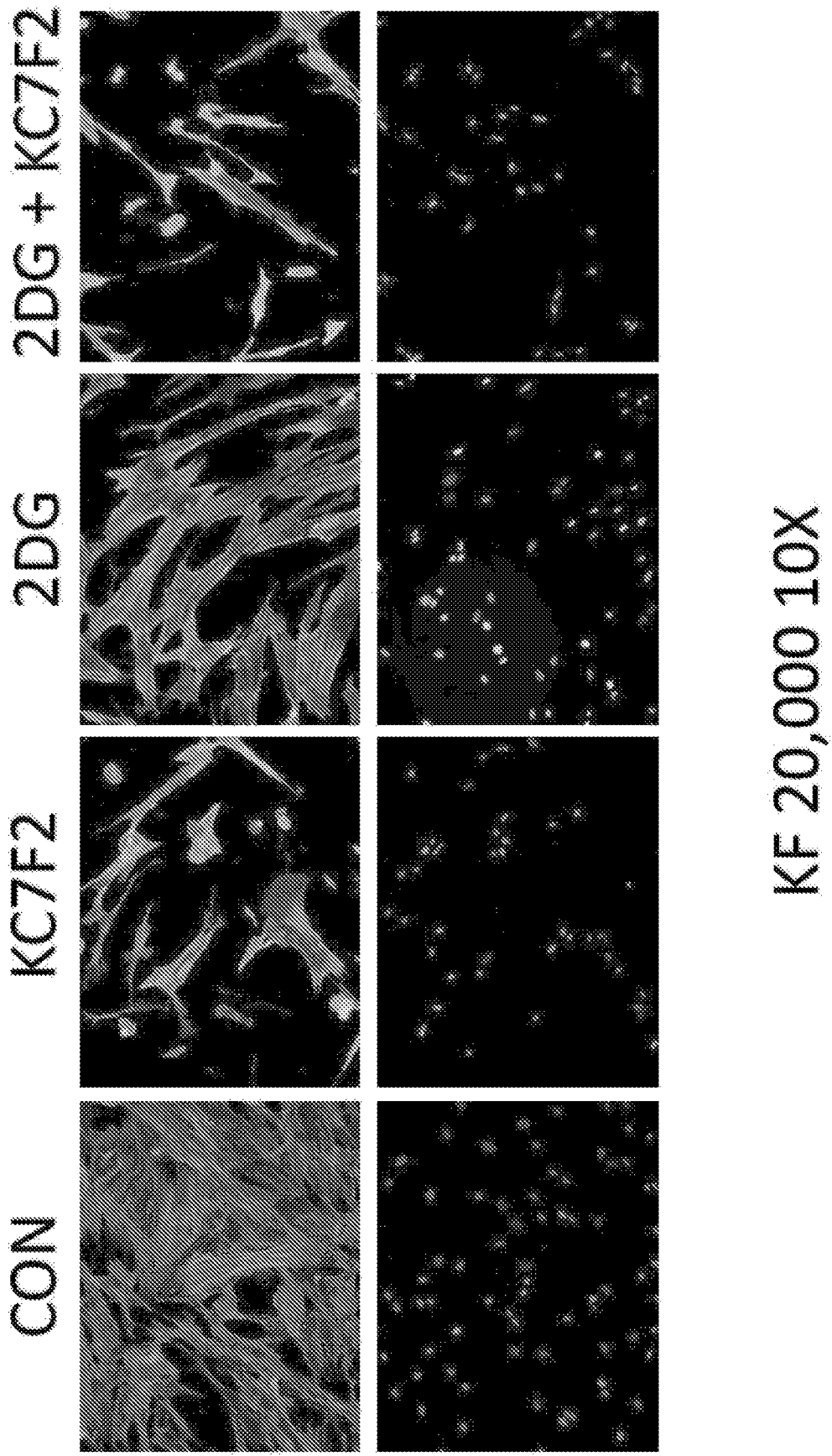
FIGS. 8A-B are fluorescent stained images showing assay results of a direct comparison between the actions of glycolytic versus HIF-1 inhibitors on keloid fibroblasts and normal fibroblasts.
Figure 8B:
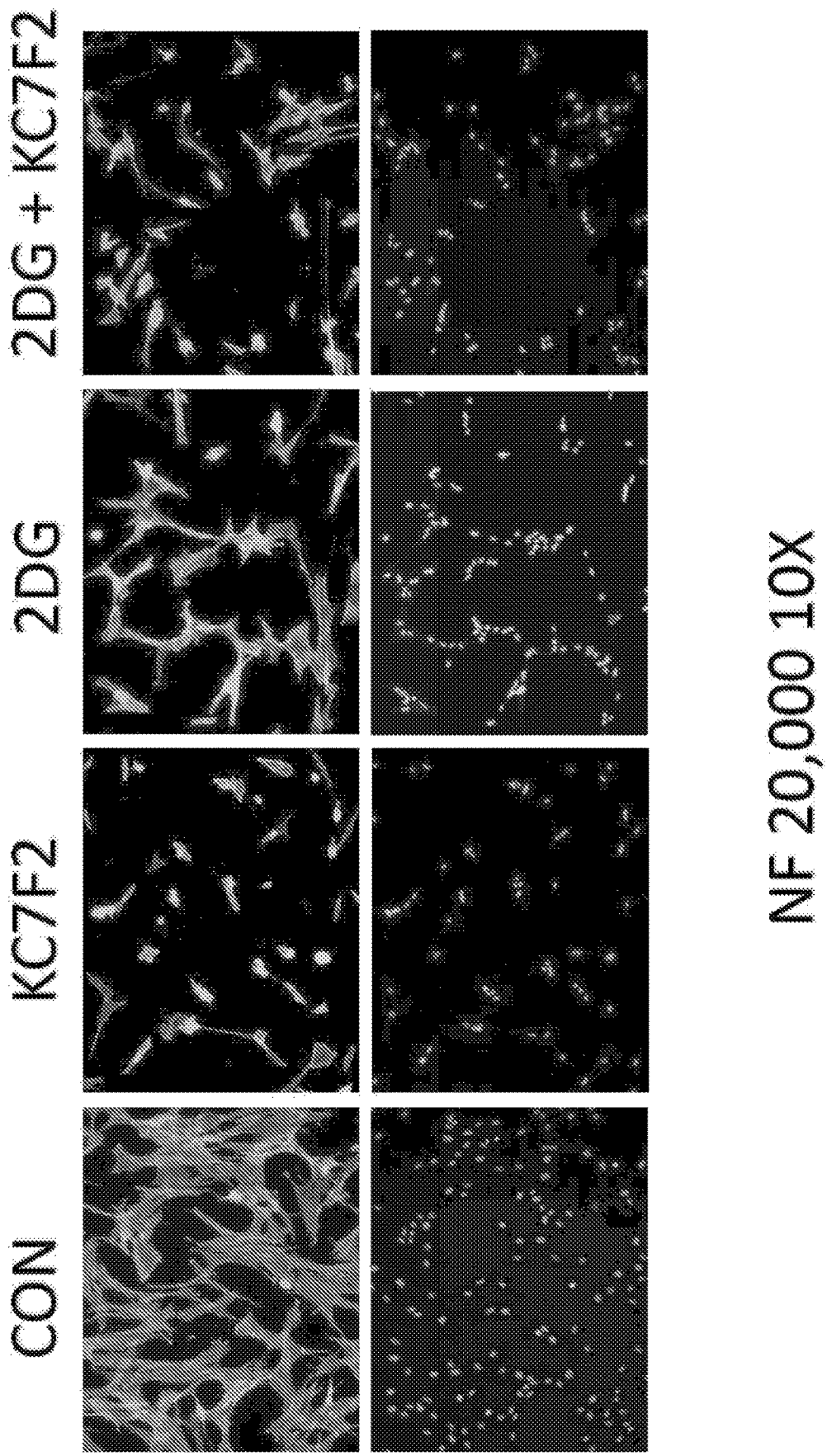

HIF-1 consists of 2 subunits: the alpha subunit, HIF-1α and the beta subunit, HIF-1β. Both subunits are expressed in every cell as mRNAs and translated into proteins. While HIF-1β is constantly present, HIF-1α is transcribed and translated, then degraded in a continual basis unless the cell or organism needs to activate hypoxia responsive genes and HIF-1 transcriptional function is therefore needed. As a result of hypoxia, the HIF-1α degradation pathway is blocked at different sites to increase the stability of HIF-1α. HIF-1α binds HIF-1β and enters the nucleus to increase the HIF-1 transcription factor's activity. Thus, HIF-1α is the regulated component that determines HIF-1 function. As shown in FIG. 3, in the presence of normoxia, prolyl-4-hydroxylase ("PHDs") hydroxylates proline residues on the von Hippel-Lindau protein ("pVHL"), which in turn binds to HIF-1α, targeting it for ubiquitination and degradation. In low oxygen states, HIF-1α accumulates, leading to transcription of genes necessary for cell survival, angiogenesis, pH regulation and cellular metabolism. Research on the cellular proteins that regulate HIF-1α stability thus provides checkpoints to modulate HIF-1 function. As discussed earlier, increasing or decreasing HIF-1 activity can have therapeutic usefulness for distinct diseases.

Currently, HIF-1α stabilizers are being developed by pharmaceutical companies such as GlaxoSmithKline (London, England) and Akebia Therapeutics (Cambridge, Mass.), among others, to provide small molecule HIF-1α inducing compounds as attractive alternatives to Amgen's (Thousand Oaks, Calif.) injectable Epogen currently on the market. These chemicals inhibit PHDs (see FIG. 3) that normally mark HIF-1α proteins for degradation. With reduced PHD function, HIF-1α proteins are stabilized and available to upregulate HIF-1 regulated genes such as EPO, which counteracts anemia. See, e.g., Mistry, N., et al., Am J Physiol Regul Integr Comp Physiol, 314(4): p. R611-R622 (2018); Liu, P., et al., ACS Med Chem Lett, 9(12): p. 1193-1198 (2018); Becker, K. A. et al., Adv Ther, 35(1): p. 5-11 (2018); Del Vecchio, L. et al., Expert Opin Investig Drugs, 27(7): p. 613-621 (2018). Conversely, to reduce HIF-1 activity, chemical HIF-1α inhibitors that block its ability to form the holoprotein, such as KC7F2, IDF-11774 or PX-478, can function to dampen the activation of HIF-1 transcriptional targets. See, Narita, T., et al., Clin Cancer Res, 15(19): p. 6128-36 (2009); Ban, H. S., et al., Bioconjug Chem. 27(8): p. 1911-20 (2016); Jacoby, J. J., et al., J Thorac Oncol, 5(7): p. 940-9 (2010); Fallah, J. et al., Curr Oncol Rep, 21(1): p. 6(2019).

The present invention provides methods for identifying compounds that induce cell death in keloids. Keloid fibroblast (KF) cells were shown to be a good model for keloid disease by testing them against normal skin fibroblasts. Under basal conditions, it was demonstrated that KFs are larger in size, express α-SMA, and exhibit elevated levels of TGF-β1 and mTORC1 activities. In the method of the present invention, equal numbers of KF cells are incubated with either a compound to be tested, a glycolysis-inhibiting compound, both the test compound and the glycolysis-inhibiting compound, and a control with no compounds added for up to sixteen (16) hours. A glycolysis inhibitor is used in the method for comparison because glycolysis-inhibiting compounds are known anti-cancer agents targeting hypoxic tumor cells. In U.S. Pat. No. 6,670,330, inhibitors of glycolysis, such as 2-deoxy-D-glucose (2-DG) are used to selectively target hypoxic tumor cells, because the hypoxic micro-environment of the slow-growing tumor cell population within solid tumors forces the tumor cells to rely primarily or exclusively on the anaerobic metabolism of glucose for survival, which distinguishes the tumor cells metabolically from the majority of the normal cells in the body that are also slow-growing but under normal oxygen tension.

One or more stains, preferably fluorescent dyes, are added to the KFs to detect dying cells. The fluorescent dyes may be Hoechst, propidium iodide, phalloidin and/or DAPI. A comparison is made of the stained dying keloid fibroblasts incubated with the test compound, with the glycolysis-inhibiting compound, and with both the test compound and the glycolysis-inhibiting compound to the control keloid fibroblasts. An increase in the number of stained dying fibroblasts compared to control indicates the test compound can induce cell death in keloids.

The present invention provides methods of treating keloids in a subject comprising administering to the subject a therapeutically effective amount of a hypoxia-inducible factor-1 (HIF-1)-inhibiting compound that induces cell death in keloids. The HIF-1 inhibiting compound can be KC7F2, IDF-11774 or PX-478. KC7F2 (N,N'-(Dithiodi-2,1-ethanediyl)bis[2,5-dichlorobenzenesulfonamide] has the molecular formula $C_{16}H_{16}Cl_4N_2O_4S_4$, a molecular weight of 570.38 and the chemical structure:

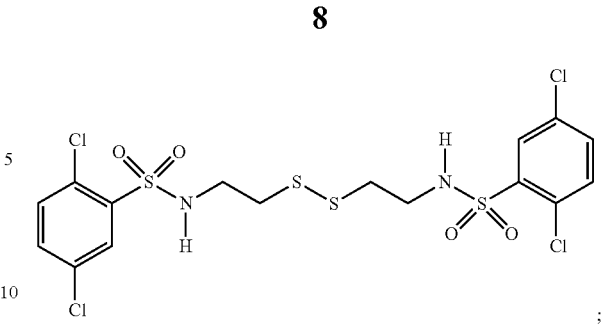

IDF-11774 (2-(4-((3r,5r,7r)-adamantan-1-yl)phenoxy)-1-(4-methylpiperazin-1-yl)ethan-1-one) has the molecular formula $C_{23}H_{32}N_2O_2$, a molecular weight of 368.51 and the chemical structure:

PX-478 2HCL ((S)-4-(2-amino-2-carboxyethyl)-N,N-bis(2-chloroethyl)aniline oxide dihydrochloride has the molecular formula $C_{13}H_{18}Cl_2N_2O_3 \cdot 2HCl$, a molecular weight of 394.12 and the chemical structure:

The HIF-1 inhibiting compound may be a pharmaceutically acceptable salt of the compound. The HIF-1 inhibiting compound can be administered in a composition further comprising at least one excipient or pharmaceutical carrier.

The method for treating keloids provided herein may reduce the keloid size in a subject by at least about 5%, 10%, 15%, 20%, 25%, 30%, 35%, 40%, 45%, 50%, 55%, 60%, 65%, 80%, 85%, 90%, 95%, 99%, or 100%, relative to the keloid size prior to administration of an HIF-1 inhibitor as assessed by methods known in the art, such as the Vancouver Scar Scale, which measures vascularity, pigmentation, pliability and height of the keloids, the Patient and Observer Scar Assessment Scale, Visual Analog Scale, and Manchester Scar Scale. See, Fearmonti R, et al. *Eplasty*. 2010 Jun. 21; 10:e43. PubMed PMID: 20596233; PubMed Central PMCID: PMC2890387. In particular embodiments, the methods for treating keloids may reduce the keloid size in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the keloid size in a subject prior to administration of an HIF-1-α inhibitor as assessed by methods known in the art.

The present invention provides methods for inducing cell death in keloids comprising contacting the keloids with a hypoxia-inducible factor-1 (HIF-1)-inhibiting compound in an amount effective to induce cell death in the keloids. The HIF-1 inhibiting compound can be KC7F2, IDF-11774 or PX-478. The keloids may be additionally contacted with a glycolysis inhibitor, such as 2-deoxyglucose (2-DG).

Definitions

Unless defined otherwise, all technical and scientific terms used herein have the same meaning as commonly understood by those of ordinary skill in the art to which this disclosure belongs. Although any methods and materials similar or equivalent to those described herein can be used in the practice or testing of the present disclosure, the preferred methods and materials are described. For purposes of the present disclosure, the following terms are defined below.

As used herein, including the appended claims, the singular form of words such as "a", "an", and "the" include their corresponding plural references unless the context appears otherwise.

The term "about" refers to ±0.5 for a numerical value.

The terms "activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

The term "activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., (catalytic activity)/(mg protein), or (immunological activity)/(mg protein), concentration in a biological compartment, or the like. "Activity" may refer to modulation of components of the innate or the adaptive immune systems.

The terms "administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human, including a human patient.

The terms "compound", "agent" and "drug" are interchangeable.

The term "comprise" and other forms of the word, such as "comprising" and "comprises," means including but not limited to, and is not intended to exclude, for example, other additives, components, integers, or steps.

The term "HIFα" refers to the alpha subunit of hypoxia inducible factor protein. HIFα may be any human or other mammalian protein, or fragment thereof, including, but not limited to, human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130, and AAB41496), and HIF-3α (Genbank Accession No. AAC72734); rat HIF-1α (Genbank Accession No. CAA70701), HIF-2α (Genbank Accession No. CAB96612), and HIF-3α (Genbank Accession No. CAB96611); and bovine HIF-1α (Genbank Accession No. BAA78675), HIF-2α (GenBank Accession No. BAA78676), and HIF-3α (Genbank Accession No. NP_001098812). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1α (Genbank Accession No. BAA34234).

The terms "HIF-1 inhibitor" or "HIF-1 inhibiting compound" means the HIF-1 inhibitor or HIF-1 inhibiting compound reduces or blockades overall HIF-1 transcriptional activity.

The term "HIF-1α stabilizer" means increasing HIF-1 activity.

The terms "hypoxia" and "hypoxic" refer to an environment with levels of oxygen below normal.

The term "increase" can refer to a level including the reference level or cut-off-value or to an overall increase of 5%, 10%, 20%, 25%, 30%, 40%, 50%, 60%, 70%, 80%, 85%, 90%, 95%, 96%, 97%, 98%, 99% or greater, in biomarker level detected by the methods described herein, as compared to the level of the same biomarker from a reference sample. In certain embodiments, the term increase refers to the increase in biomarker level, wherein the increased level is 0.1, 0.5, 1, 2, 3, 4, 5-fold or more than 5-fold higher compared to the level of the biomarker in a reference sample.

The term "decrease" can refer to a level below the reference level or cut-off-value or to an overall reduction of 5%, 10%, 20%, 25%, 30%, 40%, 50%, 60%, 70%, 80%, 85%, 90%, 95%, 96%, 97%, 98%, 99% or greater, in biomarker level detected by the methods described herein, as compared to the level of the same biomarker from a reference sample. In certain embodiments, the term decrease refers to the decrease in biomarker level, wherein the decreased level is 0.1, 0.5, 1, 2, 3, 4, 5-fold or more than 5-fold lower compared to the level of the biomarker in a reference sample.

The term "modulation" refers to modification, alteration, inhibition, regulation, activation or stimulation of the activity of a kinase protein.

The phrases "pharmaceutically acceptable" or "pharmacologically acceptable" refer to molecular entities and compositions that do not produce an adverse, toxic, allergic, inflammatory, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like that are pharmaceutically acceptable as the term is used herein and preferably inert. The use of such media and agents for pharmaceutical active substances is well known in the art. Supplementary active ingredients can also be incorporated into the compositions. Except insofar as any conventional media or agent is incompatible with the active ingredients, its use in therapeutic compositions is contemplated.

The term "therapeutically effective amount" refers to an amount of an agent, composition or drug sufficient to treat a specified disorder or disease or alternatively to obtain a pharmacological response treating a disorder or disease. Methods of determining the most effective means and dosage of administration can vary with the composition used for therapy, the purpose of the therapy, the target cell being treated, and the subject being treated. Treatment dosages generally may be titrated to optimize safety and efficacy. Single or multiple administrations can be carried out with the dose level and pattern being selected by the treating physician. When the compounds described herein are co-administered with another agent or therapy, the effective amount may be less than when the agent is used alone. Suitable dosage formulations and methods of administering the agents can be readily determined by those of skill in the art. For example, a compound described herein may be administered in an amount from 0.1 to 50 mg/kg per day. A therapeutically effective amount may vary depending on the compound, the disorder and its severity and the age, weight, physical condition and responsiveness of the subject to be treated.

The terms "treat" or "treating" means to administer a therapeutic agent, such as a composition containing any of the HIF-1 inhibiting compounds of the present invention, internally or externally to a subject or patient having one or more disease symptoms, or being suspected of having a disease or being at elevated at risk of acquiring a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient, and the ability of the drug to elicit a desired response in the subject Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

The term "treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses transfection of any of the HIF-1 inhibiting compounds or related methods of the present invention as applied to a human or animal subject, a cell, tissue, physiological compartment, or physiological fluid.

The benefit to a subject to be treated is either statistically significant or at least perceptible to the patient or to the physician.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the disclosure can be administered. In an exemplary embodiment of the present disclosure, to identify subject patients for treatment according to the methods of the disclosure, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present disclosure.

For the purposes of the present disclosure the term "excipient" and "carrier" are used interchangeably throughout the description of the present disclosure and said terms are defined herein as, "ingredients which are used in the practice of formulating a safe and effective pharmaceutical composition."

Compositions and Formulations

Excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach.

The present disclosure also provides administration of pharmaceutical compositions that include at least one HIF-1 inhibiting-compound described herein and one or more pharmaceutically acceptable carriers, excipients, or diluents. Pharmaceutically acceptable excipients include any pharmaceutical agent that does not itself induce the production of antibodies harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991). Pharmaceutically acceptable carriers are those that are compatible with the other ingredients in the formulation and are biologically acceptable. Supplementary active ingredients can also be incorporated into the pharmaceutical compositions.

Compounds of the present disclosure can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known HIF inhibitors. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present disclosure can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and *arachis* oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Delivery vehicles such as liposomes, nanocapsules, microparticles, microspheres, lipid particles, vesicles, and the like, may be used for the introduction of the compositions of the present invention into suitable host cells.

In certain embodiments, the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present disclosure can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

Compounds described herein can be administered parenterally or intraperitoneally. The compounds of the present disclosure can also be administered topically or by intralesional administration to the keloids. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present disclosure including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Lipid formulations or nanocapsules can be used to introduce compounds of the present disclosure into host cells either in vitro or in vivo. Lipid formulations and nanocapsules can be prepared by methods known in the art.

In certain embodiments, it can be desirable to a compound is combined with other agents effective in the treatment of the target disease to increase the effectiveness of compounds of the present disclosure. For example, other active compounds (i.e., other active ingredients or agents) effective in treating the target disease can be administered with compounds of the present disclosure. The other agents can be administered at the same time or at different times than the compounds disclosed herein.

Compounds of the present disclosure can be useful for the treatment or inhibition of a pathological condition or disorder in a mammal, for example, a human subject. The present disclosure accordingly provides methods of treating or inhibiting a pathological condition or disorder by providing to a mammal a compound of the present disclosure including its pharmaceutically acceptable salt) or a pharmaceutical composition that includes one or more compounds of the present disclosure in combination or association with pharmaceutically acceptable carriers. Compounds of the present disclosure can be administered alone or in combination with other therapeutically effective compounds or therapies for the treatment or inhibition of the pathological condition or disorder.

Pharmaceutically acceptable salts of compounds of the present disclosure, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na2CO3$, $KHCO3$, $K2CO3$, $Cs2CO3$, $LiOH$, $NaOH$, $KOH$, $NaH2PO4$, $Na2HPO4$, and $Na3PO4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

Dosage treatment may be a single dose schedule or a multiple dose schedule to ultimately deliver the amount specified above. Moreover, the subject may be administered as many doses as appropriate. One of skill in the art can readily determine an appropriate number of doses to administer.

The present disclosure may be better understood by reference to the following non-limiting examples, which are presented in order to more fully illustrate the preferred embodiments of the disclosure. They should in no way be construed to limit the scope of the disclosure.

EXAMPLES

Example 1

Keloid fibroblast (KF) cells (CRL1762) and normal skin fibroblasts (NF, CRL2439) were both purchased from the American Type Culture Collection (ATCC, Manassas, Va.). Under basal conditions, the KFs are larger in size, express α-SMA, and exhibit elevated levels of TGF-β1 and mTORC1 activities. These KF cells display a slower growth rate and are particularly sensitive to glucose deprivation, confirming a reliance on glycolytic metabolism. To test the hypothesis that HIF-1 function plays an important role in KF biology, three structurally distinct chemical inhibitors, KC7F2, IDF-11774, and PX-478 that differ in their mechanisms of action, were chosen to examine the cellular consequences of HIF-1 functional blockade.

In this assay direct comparison between the actions of glycolytic versus HIF-1 inhibitors was facilitated. For each human skin fibroblast, an equal number of cells were plated per well. Each well was treated and incubated for 16 hours with the following: Control, no chemical treatment; 40 μM KC7F2; 10 mM 2-deoxyglucose (2-DG), a glycolysis inhibitor; both 40 μM KC7F2 and 10 mM 2-DG; 25 uM IDF-11774; and 25 uM PX-478. Cell nuclei were then labelled with Hoechst and cells were labelled propidium iodide to indicate dying cells.

The results are shown in FIGS. 4A-D. It was found that the presence of the HIF-1 inhibitor correlated with more PI-positive dying cells in KF wells, while reducing the total number of cells in both NF and KF wells compared to the control untreated cells. In contrast, despite the importance of aerobic glycolysis in KFs, the use of 2-DG alone, was insufficient to impede proliferation to an appreciable amount. KC7F2 alone reduced the number of KF cells consistently and the best compared to IDF-11774 and PX-478. IDF-11774 worked less well, but showed the same trend. PX-478 did not work well, but might work at higher doses. KCF72 in combination with the glycolysis inhibitor, 2-DG, reduced the number of KF cells, but not as effectively as KCF72 alone.

Example 2

Keloid fibroblast (KF) cells (CRL1762) and normal skin fibroblasts (NF, CRL2439) were both purchased from the American Type Culture Collection (ATCC, Manassas, Va.). This assay compared the effects of KC7F2 versus the glycolytic inhibitor 2-DG on the cellular consequences of HIF-1 functional blockade.

For each human skin fibroblast, 10,000 cells were plated per well. Each well was treated and incubated for 16 hours with the following: Control, no chemical treatment; 40 µM KC7F2; 10 mM 2-deoxyglucose (2-DG), a glycolysis inhibitor; and both 40 µM KC7F2 and 10 mM 2-DG. Cells were stained with phalloidin for filamentous actin and cells were labelled DAPI (4',6-diamidino-2-phenylindolepropridium iodide) to indicate dying cells. Images were taken at a magnification of 4 times (4×) and 10 times (10×).

The results are shown in FIGS. 5A-B and 6A-B. It was found that the presence of the HIF-1 inhibitor correlated with more DAPI-positive dying cells and reduced filamentous actin in KF wells, while reducing the total number of cells in both NF and KF wells compared to the control untreated cells. In contrast, the use of 2-DG alone was insufficient to impede proliferation to an appreciable amount. KC7F2 alone reduced the number of KF cells consistently and the best compared to KCF72 in combination with 2-DG.

Example 3

Keloid fibroblast (KF) cells (CRL1762) and normal skin fibroblasts (NF, CRL2439) were both purchased from the American Type Culture Collection (ATCC, Manassas, Va.). This assay compared the effects of KC7F2 versus the glycolytic inhibitor 2-DG on the cellular consequences of HIF-1 functional blockade.

For each human skin fibroblast, 20,000 cells, were plated per well. Each well was treated and incubated for 16 hours with the following: Control, no chemical treatment; 40 µM KC7F2; 10 mM 2-deoxyglucose (2-DG), a glycolysis inhibitor; and both 40 µM KC7F2 and 10 mM 2-DG. Cells were stained with phalloidin for filamentous actin and cells were labelled DAPI (4',6-diamidino-2-phenylindolepropridium iodide) to indicate dying cells. Images were taken at a magnification of 4 times (4×) and 10 times (10×).

The results are shown in FIGS. 7A-B and 8A-B. It was found that the presence of the HIF-1 inhibitor correlated with more DAPI-positive dying cells and reduced filamentous actin in KF wells, while reducing the total number of cells in both NF and KF wells compared to the control untreated cells. In contrast, the use of 2-DG alone was insufficient to impede proliferation to an appreciable amount. KC7F2 alone reduced the number of KF cells consistently and the best compared to KCF72 in combination with 2-DG.

Example 4

To further establish the therapeutic usefulness of HIF-1 blockade in the treatment of keloid disease, the effects of HIF-1 chemical inhibitors on KF and NF viability are measured using highly sensitive assays.

To determine whether HIF-1 inhibition leads to KF apoptosis, Annexin V Apoptosis and Necrosis Assay is performed to demonstrate that HIF-1 inhibiting compounds are not just toxic to the cell, making them necrotic, but are inducing apoptosis in the cells. The ability to induce apoptosis in pathological KF cells would be the desired outcome of a keloid-targeted therapy.

The methodology for the Annexin V Apoptosis and Necrosis Assay, available from Promega (Madison, Wis.) (Product No. JA1000) is provided below.

Immediately before preparing the 2×Detection Reagent, thaw the Annexin V NanoBiT® Luciferase Substrate, CaCl2 and Necrosis Detection Reagent, a cell-impermeant, pro-fluorescent DNA dye, at room temperature and place the annexin v fusion proteins Annexin V-SmBiT and Annexin V-LgBiT on ice. Briefly centrifuge all kit components after thawing to facilitate maximum recovery. Harvest cells (attachment-dependent or attachment-independent) and resuspend the cell pellet to 200,000 cells/ml in prewarmed complete medium.

Add 50 µl of 200,000 cells/ml to wells A1-H11 in a 96-well plate (10,000 cells/well). Add 50 µl of complete cell culture medium (no cells) to column 12 for a 96-well plate. This column will be the no-cells, no-compound control.

Using the appropriate 12-channel trough and a 12-channel multichannel pipette, transfer 50 µl of the appropriate 4× concentrated, 10-point, twofold serial dilution to the appropriate replicate wells in the 96-well assay plate containing cells. Add the control compound to replicate wells in rows A-D and test compound to replicate wells in rows E-H. Each well should now contain 100 µl. Add the compound titration series from high to low concentration (highest concentration to lowest concentration from column 1 to column 10). Columns 11 and 12 should contain no compound (vehicle controls).

Prepare 2× Detection Reagent. Add 100 µl of the 2× Detection Reagent in complete medium to all wells in the 96-well assay plate. All wells should now contain a final assay volume of 200 µl for a 96-well plate. Shake the assay plate on a plate shaker for approximately 30 seconds at 500-700 rpm to mix. Incubate and record luminescence and fluorescence measurements.

Example 5

To further establish the therapeutic usefulness of HIF-1 blockade in the treatment of keloid disease, the effects of HIF-1 chemical inhibitors on KF and NF viability are measured using highly sensitive assays.

To determine whether HIF-1 inhibition leads to KF apoptosis, the TUNEL (terminal deoxynucleotidyl transferase dUTP nick end labeling) assay for detection of apoptotic cells in situ is performed to demonstrate that HIF-1 inhibiting compounds are not just toxic to the cell, making them necrotic, but are inducing apoptosis in the cells. The ability to induce apoptosis in pathological KF cells would be the desired outcome of a keloid-targeted therapy.

The Colorimetric Tunel System Assay, available from Promega (Madison, Wis.) (Product No. G7360) end-labels the fragmented DNA of apoptotic cells using a modified TUNEL method. Biotinylated nucleotide is incorporated at the 3"-OH DNA ends using the Terminal Deoxynucleotidyl Transferase, Recombinant, (rTdT) enzyme. Horseradish peroxidase-labeled streptavidin (Streptavidin HRP) is then bound to these biotinylated nucleotides, which are detected using the stable chromogen, diaminobenzidine (DAB). Using this procedure, apoptotic nuclei are stained dark brown and visualized with a light microscope.

The methodology for the Colorimetric Tunel System Assay, available from Promega (Madison, Wis.) (Product No. G7360) is provided below.

To detect apoptosis, first immerse slides in 10% buffered formalin or 4% paraformaldehyde for 25 minutes. Immerse slides twice in PBS, 5 minutes each time. Immerse slides in 0.2% Triton® X-100 in PBS for 5 minutes. Immerse slides twice in PBS, 5 minutes each time. Add 100 µl Equilibration Buffer. Equilibrate at room temperature for 5-10 minutes.

Add 100 µl of TdT reaction mix to the cells on the slides. Do not allow cells to dry completely. Cover slides with Plastic Coverslips to ensure even distribution of the mix. Incubate slides for 60 minutes at 37° C. in a humidified chamber. Remove Plastic Coverslips. Immerse slides in 2×SSC for 15 minutes. Immerse slides three times in PBS, 5 minutes each time. Immerse slides in 0.3% hydrogen peroxide for 3-5 minutes. Immerse slides three times in PBS, 5 minutes each time. Add 100 µl Streptavidin HRP (diluted 1:500 in PBS). Incubate slides for 30 minutes at room temperature. Immerse slides three times in PBS, 5 minutes each time.

Add 100 µl DAB Solution (prepare immediately prior to use by adding 100 µl DAB 10× Chromogen to 900 µl DAB Substrate 1× Buffer). Develop until a light brown background appears. Do not allow the background to become too dark. Immerse slides several times in deionized water. Mount slides in an aqueous or permanent mounting medium. Observe staining with a light microscope.

REFERENCES

1. Atwal, P. S., et al., Novel X-linked syndrome of cardiac valvulopathy, keloid scarring, and reduced joint mobility due to filamin A substitution G1576R. Am J Med Genet A, 2016. 170A(4): p. 891-5.
2. Curtis, K. K., W. W. Wong, and H. J. Ross, Past approaches and future directions for targeting tumor hypoxia in squamous cell carcinomas of the head and neck. Crit Rev Oncol Hematol, 2016. 103: p. 86-98.
3. Tiffany, L. M., Comparison between the surgical diseases of the white and colored races. Transactions of the American Surgical Association, 1887. V: p. 262-273.
4. Trace, A. P., et al., Keloids and Hypertrophic Scars: A Spectrum of Clinical Challenges. Am J Clin Dermatol, 2016. 17(3): p. 201-23.
5. Shi, C., J. Zhu, and D. Yang, The pivotal role of inflammation in scar/keloid formation after acne. Dermatoendocrinol, 2017. 9(1): p. e1448327.
6. Mari, W., et al., Novel Insights on Understanding of Keloid Scar: Article Review. J Am Coll Clin Wound Spec, 2015. 7(1-3): p. 1-7.
7. Shih, B. and A. Bayat, Genetics of keloid scarring. Arch Dermatol Res, 2010. 302(5): p. 319-39.
8. Shih, B., et al., Molecular dissection of abnormal wound healing processes resulting in keloid disease. Wound Repair Regen, 2010. 18(2): p. 139-53.
9. Nakashima, M., et al., A genome-wide association study identifies four susceptibility loci for keloid in the Japanese population. Nat Genet, 2010. 42(9): p. 768-71.
10. Zhu, F., et al., Association study confirmed susceptibility loci with keloid in the Chinese Han population. PLoS One, 2013. 8(5): p. e62377.
11. Lu, W., et al., SNP rs1511412 in FOXL2 gene as a risk factor for keloid by meta analysis. Int J Clin Exp Med, 2015. 8(2): p. 2766-71.
12. Velez Edwards, D. R., et al., Admixture mapping identifies a locus at 15q21.2-22.3 associated with keloid formation in African Americans. Hum Genet, 2014. 133(12): p. 1513-23.
13. Zhao, Y., et al., NEDD4 single nucleotide polymorphism rs2271289 is associated with keloids in Chinese Han population. Am J Transl Res, 2016. 8(2): p. 544-55.
14. Sun, L. M., K. H. Wang, and Y. C. Lee, Keloid incidence in Asian people and its comorbidity with other fibrosis-related diseases: a nationwide population-based study. Arch Dermatol Res, 2014. 306(9): p. 803-8.
15. Robles, D. T. and D. Berg, Abnormal wound healing: keloids. Clin Dermatol, 2007. 25(1): p. 26-32.
16. Werner, S., T. Krieg, and H. Smola, Keratinocyte-fibroblast interactions in wound healing. J Invest Dermatol, 2007. 127(5): p. 998-1008.
17. Arwert, E. N., E. Hoste, and F. M. Watt, Epithelial stem cells, wound healing and cancer. Nat Rev Cancer, 2012. 12(3): p. 170-80.
18. Audrito, V., et al., PD-L1 up-regulation in melanoma increases disease aggressiveness and is mediated through miR-17-5p. Oncotarget, 2017. 8(9): p. 15894-15911.
19. Babu, M., R. Diegelmann, and N. Oliver, Keloid fibroblasts exhibit an altered response to TGF-beta. J Invest Dermatol, 1992. 99(5): p. 650-5.
20. Bettinger, D. A., et al., The effect of TGF-beta on keloid fibroblast proliferation and collagen synthesis. Plast Reconstr Surg, 1996. 98(5): p. 827-33.
21. Syed, F., et al., Potent dual inhibitors of TORC1 and TORC2 complexes (KU-0063794 and KU-0068650) demonstrate in vitro and ex vivo anti-keloid scar activity. J Invest Dermatol, 2013. 133(5): p. 1340-50.
22. Syed, F., et al., Keloid disease can be inhibited by antagonizing excessive mTOR signaling with a novel dual TORC1/2 inhibitor. Am J Pathol, 2012. 181(5): p. 1642-58.
23. Li, Q., et al., Metabolic reprogramming in keloid fibroblasts: Aerobic glycolysis and a novel therapeutic strategy. Biochem Biophys Res Commun, 2018. 496(2): p. 641-647.
24. Vincent, A. S., et al., Human skin keloid fibroblasts display bioenergetics of cancer cells. J Invest Dermatol, 2008. 128(3): p. 702-9.
25. Hanahan, D. and R. A. Weinberg, Hallmarks of cancer: the next generation. Cell, 2011. 144(5): p. 646-74.
26. Ikeda, K., et al., Resveratrol inhibits fibrogenesis and induces apoptosis in keloid fibroblasts. Wound Repair Regen, 2013. 21(4): p. 616-23.
27. Si, L. B., et al., Sensitization of keloid fibroblasts by quercetin through the PI3K/Akt pathway is dependent on regulation of HIF-1alpha. Am J Transl Res, 2018. 10(12): p. 4223-4234.
28. Mistry, N., et al., Red blood cell antibody-induced anemia causes differential degrees of tissue hypoxia in kidney and brain. Am J Physiol Regul Integr Comp Physiol, 2018. 314(4): p. R611-R622.
29. Liu, P., et al., Discovery of Orally Bioavailable and Liver-Targeted Hypoxia-Inducible Factor Prolyl Hydroxylase (HIF-PHD) Inhibitors for the Treatment of Anemia. ACS Med Chem Lett, 2018. 9(12): p. 1193-1198.
30. Becker, K. A. and J. J. Jones, An Emerging Treatment Alternative for Anemia in Chronic Kidney Disease Patients: A Review of Daprodustat. Adv Ther, 2018. 35(1): p. 5-11.
31. Del Vecchio, L. and F. Locatelli, Investigational hypoxia-inducible factor prolyl hydroxylase inhibitors (HIF-PHI) for the treatment of anemia associated with chronic kidney disease. Expert Opin Investig Drugs, 2018. 27(7): p. 613-621.
32. Narita, T., et al., Identification of a novel small molecule HIF-1alpha translation inhibitor. Clin Cancer Res, 2009. 15(19): p. 6128-36.
33. Ban, H. S., et al., Identification of Targets of the HIF-1 Inhibitor IDF-11774 Using Alkyne-Conjugated Photoaffinity Probes. Bioconjug Chem, 2016. 27(8): p. 1911-20.
34. Jacoby, J. J., et al., Treatment with HIF-1alpha antagonist PX-478 inhibits progression and spread of orthotopic human small cell lung cancer and lung adenocarcinoma in mice. J Thorac Oncol, 2010. 5(7): p. 940-9.
35. Fallah, J. and B. I. Rini, HIF Inhibitors: Status of Current Clinical Development. Curr Oncol Rep, 2019. 21(1): p. 6.
36. Fearmonti R, Bond J, Erdmann D, Levinson H. A review of scar scales and scar measuring devices. *Eplasty.* 2010 Jun. 21; 10:e43. PubMed PMID: 20596233; PubMed Central PMCID: PMC2890387.
37. https://www.promega.com/Products/Cell-Health-Assays/Apoptosis-Assays/RealTime%20Glo%20Annexin%20V%20Apoptosis%20Assay/?fq=JA1000&catNum=JA1000
38. https://www.promega.com/Products/Cell-Health-Assays/Apoptosis-Assays/DeadEnd-Colorimetric-TUNEL-System/?fq=tunel&catNum=G7360

What is claimed is:

1. A method of treating a human subject having keloids comprising administering to the human subject in need thereof a therapeutically effective amount of a hypoxia-inducible factor-1 (HIF-1)-inhibiting compound, wherein the therapeutically effective amount is determined in an assay to induce cell death in keloids.

2. The method of claim 1, wherein the HIF-1 inhibiting compound is selected from the group consisting of N,N'-(Dithiodi-2, 1-ethanediyl)bis[2,5-dichlorobenzenesulfonamide (KC7F2), 2-(4-((3r,5r,7r)-adamantan-1-yl)phenoxy)-1-(4-methylpiperazin-1-yl)ethan-1-one (IDF-11774), (S)-4-(2-amino-2-carboxyethyl)-N,N-bis(2-chloroethyl)aniline oxide dihydrochloride (PX-478), and a pharmaceutically acceptable salt thereof.

3. The method of claim 1, wherein the HIF-1 inhibiting compound is administered in a composition further comprising at least one excipient or pharmaceutical carrier.

4. The method of claim 1, further comprising administering a glycolysis inhibitor.

5. The method of claim 4, wherein the glycolysis inhibitor is 2-deoxyglucose (2-DG).

6. A method of inducing cell death in keloids comprising contacting the keloids with a hypoxia-inducible factor-1 (HIF-1)-inhibiting compound in an amount effective to induce cell death in the keloids, wherein the effective amount is determined in an assay to induce cell death in keloids.

7. The method of claim 6, wherein the HIF-1 compound is selected from the group consisting of N,N'-(Dithiodi-2,1-ethanediy 1)bis[2,5-dichlorobenzenesulfonamide (KC7F2), 2-(4-((3r,5r,7r)-adamantan-1-yl)phenoxy)-1-(4-methylpiperazin-1-yl)ethan-1-one (IDF-11774), (S)-4-(2-amino-2-carboxyethyl)-N,N-bis(2-chloroethyl)aniline oxide dihydrochloride (PX-478), and a pharmaceutically acceptable salt thereof.

8. The method of claim 6, further comprising contacting the keloids with a glycolysis inhibitor in an amount effective to induce cell death in the keloids.

9. The method of claim 8, wherein the glycolysis inhibitor is 2-deoxyglucose (2-DG).

10. The method of claim 1, wherein the HIF-1-inhibiting compound blocks the ability of HIF-1α to form a holoprotein.

11. The method of claim 6, wherein the HIF-1-inhibiting compound blocks the ability of HIF-1α to form a holoprotein.

* * * * *